US008137903B2

United States Patent
Kaufman et al.

(10) Patent No.: US 8,137,903 B2
(45) Date of Patent: Mar. 20, 2012

(54) METHOD FOR MAGNETIC SEPARATION OF RED BLOOD CELLS FROM A PATIENT SAMPLE

(75) Inventors: Howie Kaufman, Newton, MA (US); Lawrence Burg, Framingham, MA (US)

(73) Assignee: Cytyc Corporation, Marlborough, MA (US)

( * ) Notice: Subject to any disclaimer, the term of this patent is extended or adjusted under 35 U.S.C. 154(b) by 381 days.

(21) Appl. No.: 12/335,748

(22) Filed: Dec. 16, 2008

(65) Prior Publication Data

US 2011/0104778 A1     May 5, 2011

Related U.S. Application Data

(60) Provisional application No. 61/015,335, filed on Dec. 20, 2007.

(51) Int. Cl.
   *B01D 35/06*     (2006.01)
   *A01N 1/02*     (2006.01)
   *G01N 33/553*     (2006.01)
(52) U.S. Cl. .......................................... 435/2; 210/695
(58) Field of Classification Search ........................ None
See application file for complete search history.

(56) References Cited

U.S. PATENT DOCUMENTS

| 5,837,144 A | * | 11/1998 | Bienhaus et al. | ............. | 210/695 |
| 2006/0024824 A1 | * | 2/2006 | Woodside et al. | ............ | 435/366 |

FOREIGN PATENT DOCUMENTS

| JP | 2001-147226 | * | 5/2001 |
| WO | WO98/18005 | | 4/1998 |

OTHER PUBLICATIONS

Sweeney et al., "Comparison of the Effectiveness of Two Liquid-Based Papanicolaou Systems in the Handling of Adverse Limiting Factors, such as Excessive Blood", Cancer (Cancer Cytopathology) 108 (1) : 27-31 (2006).*
Lam et al., "Minimizing red blood cell contamination while isolating mononuclear cells from whole blood: The next step for the treatment of severe hemolytic disease of the fetus/newborn", American J. Obstet. Gynecol. 189 (4) : 1012-1016 (2003).*
International Preliminary Report on Patentability and Written Opinion from related PCT Application No. PCT/US2008/086972 dated Jul. 1, 2010.
Haik Y, et al. "Development of Magnetic Device for Cell Separation" Journal of Magnetism and Magnetic Materials, vol. 194, No. 1-3, Apr. 1, 1999, p. 254-261.

* cited by examiner

*Primary Examiner* — Sandra Saucier

(57) ABSTRACT

A method for separating components from a patient sample is provided. In particular, the present invention provides a method for the separation of red blood cells or red blood cell components from a patient sample by the use of magnetic beads.

16 Claims, 3 Drawing Sheets

METHOD FOR MAGNETIC SEPARATION OF RED BLOOD CELLS FROM A PATIENT SAMPLE

This application claims priority to provisional application 61/015,335 filed Dec. 20, 2007.

FIELD OF THE INVENTION

A method for separating components from a patient sample is provided. In particular, the present invention provides a method for the separation of red blood cells or red blood cell components from a patient sample by the use of magnetic beads.

A BACKGROUND OF THE INVENTION

The use of magnetic beads for the separation of components from biological samples has many precedents and is well documented (Kvam et al., Application of Magnetic Beads in Bioassays; Bio/Technology 11, 60-63 (1993)). In particular, the use of magnetic beads for the separation of target antigens from biological fluids for diagnostic purposes is especially useful where the biological fluid is a whole blood.

Cytology generally refers to the study of the structure, function and pathology of cells. In a clinical laboratory environment cytotechnologists and pathologists diagnose a patient's condition by visually examining specimens of the patient's cells. These cells are typically stained to better define the structure of the cells and to aid in the visual review of the cells.

One common cytological technique is a pap smear, in which the cells from a woman's cervix are sampled and analyzed in order to detect the presence of abnormal cells. The process involves collecting a specimen from a woman's cervix using a brush or related instruments, and the specimen is then transferred to a slide for subsequent processing. The slide containing the specimen is then stained using on or more staining solutions and the slides are then coverslipped. The slide can then be evaluated visually by a cytotechnologist or by an automated imaging system. The presence of blood or other macromolecules in the patient sample may result in a scant cellular material on the prepared slide thus rendering the slide unusable for diagnostic purposes.

Accordingly, there is a need in the art for improved methods for separating biological components from a patient sample. In particular, present invention relates to a means by which red blood cells or red blood cell components are separated from a patient sample by the use of magnetic beads. The present invention fulfills these needs and further provides other related advantages.

SUMMARY OF THE INVENTION

Figure 1:
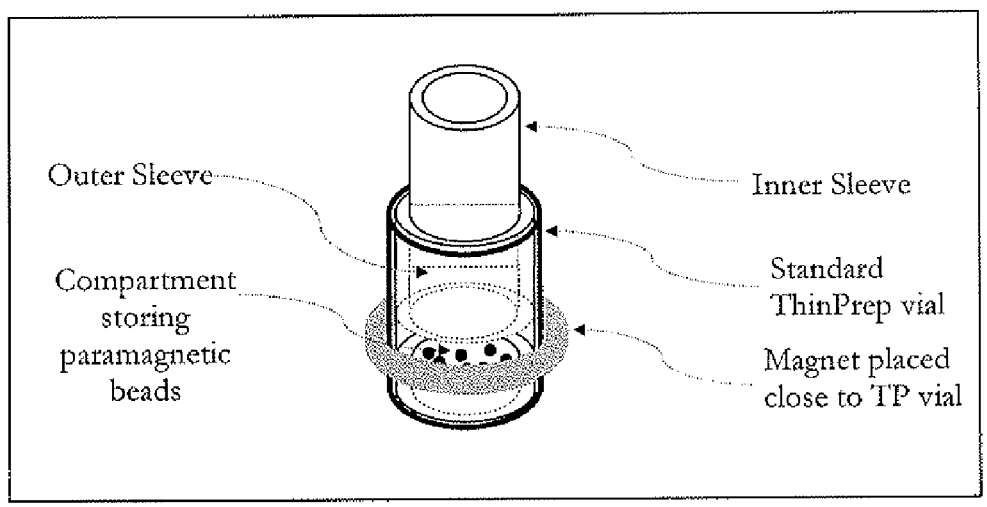
FIG. 1. is an illustration of a first assembly device in accordance with one or more aspects of the present invention FIG. 2. is an illustration of the arrangement of an Inner Sleeve, an Outer Sleeve and a standard ThinPrep vial in accordance with one or more aspects of the present invention FIG. 3. is an illustration of a method to release paramagnetic beads, retrieve paramagnetic beads, and physically immobilize paramagnetic beads in accordance with one or more aspects of the present invention

The present invention generally relates to a method of separating red blood cells or red blood cell fragments from other components of a biological sample in a specimen container. In one aspect of the present invention, a method comprising the steps of adding a complex comprising magnetic beads and a binder to a biological sample in a specimen container containing red blood cells or red blood cell fragments allowing the complex to selectively bind to the red blood cells or red blood cell fragments in the specimen container; positioning a magnetic field in close proximity to the magnetic beads in the specimen container such that the beads are manipulated by the magnetic field; and manipulating the beads such that the red blood cells or red blood cell fragments separate from other cellular components of the patient sample in the specimen container is provided.

In another aspect of the present invention, a method of separating red blood cells or red blood cell fragments from other cellular components in specimen container containing cells of a patient specimen suspended in a specimen fluid, the method comprising the steps of, adding a complex comprising magnetic beads and a binder which specifically binds to hemoglobin to a vial containing cells of a patient specimen suspended in a specimen fluid and red blood cells or red blood cell fragments, allowing the complex to selectively bind to hemoglobin in the red blood cells or red blood cell fragments and positioning a magnetic field in close proximity to the complex such that the complex move towards the magnet field is provided.

In yet another aspect of the present invention, a method of separating red blood cells or red blood cell fragments from other cellular components in specimen container containing cervical cells suspended in a preservative fluid, the method comprising the steps of, adding a complex comprising magnetic beads with aptamers specific to hemoglobin bound thereto to a specimen container containing cervical cells suspended in a preservative solution fluid and red blood cells or red blood cell fragments, allowing the complex to selectively bind to hemoglobin in the red blood cells or red blood cell fragments and positioning a magnet in close proximity to the complex such that the complex move towards the magnet; whereby the movement of the complex towards the magnetic results in the red blood cells or red blood cell fragments separating from other cellular components of the patient specimen suspended in the fluid in the specimen container is provided.

DEFINITIONS

As used herein, the following terms have the meanings ascribed to them unless specified otherwise.

As used herein, the term binder is defined as a compound that selectively binds to a particular molecule or class of molecules. The class of molecules that a binder can bind to includes, but is not limited to, proteins, nucleic acid molecules, carbohydrates, lipids, ligands, drugs, ions and any other molecules that can specifically bind to a particular compound. A particular example of a binder is an aptamer.

As used herein, the term biological sample is defined as a biological or body fluid sample or a biological tissue sample. Examples of biological or body fluid samples include urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage or samples derived therefrom (e.g., reagent-modified and/or fractionated samples). Urine samples can be neat or frozen. Fluid samples can be analyzed as it is being provided (e.g., a urine stream dipstick), can be collected in a container, or can be collected with a swab. Exemplary swab samples include cervicovaginal swab samples, including, but not limited to swab of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof. Biological tissue samples are samples containing an aggregate of cells, usually of a particular kind, together with intercellular substances that form one of the structural materials of a human, animal, plant, bacterial, fungal or viral structure, including connective, epithelium, muscle and nerve tissues. Examples of biological tissue samples also include organs (e.g., breasts), tumors, lymph nodes, arteries and individual cell(s). For example, the sample can be a tissue sample suspected of being cancerous. Reference herein to any of the above fluid types or any tissue or cell sample also includes reagent-modified and fractionated samples. Thus, reference to a cervical sample also includes a buffer-treated cervical sample, and reference to a tissue sample includes the supernatant from a homogenate of that tissue.

As used herein, the term cell preservative solution is defined as an alcohol based solution (e.g., methanol, ethanol, isopropanol) from 20% to 95% (v/v) with or without other additives such as polyethylene glycol and formaldehyde. For example, PreservCyt®, (Hologic, Marlborough, Mass.), is a methanol-based, buffered, solution designed to support cells during transport and microscope slide preparation with the ThinPrep® Processor. There are several types of saline or balanced salt, alcohol-free solutions are commercially available for preserving cell specimens includes Hanks' balanced salt solution, a minimal essential tissue culture medium (MEM), and normal saline.

As used herein, the term complex is defined as a complex that includes a binding partner bound to a moiety, where the binding between the binding partner and the moiety can arise from one or more covalent bonds or non-covalent interactions such as hydrogen bonds, or electrostatic interactions.

As used herein, the term paramagnetic is defined as being or relating to a magnetizable substance that has a small but positive susceptibility which varies little with magnetizing force As used herein, the term patient sample is defined as a biological sample taken from any animal for whom diagnosis, screening, monitoring or treatment is contemplated. Animals include mammals such as primates and domesticated animals. An exemplary primate is human. A patient refers to a subject such as a mammal, primate, human or livestock subject afflicted with a disease condition or for which a disease condition is to be determined or risk of a disease condition is to be determined.

As used herein, the term selectively bind is defined as the selective binding of a binding partner to the binding of a binding partner to a particular molecule with at least about 2-fold and typically at least about 5-fold, 10-fold, 50-fold, 100-fold, or more, greater affinity ($K_a$ or $K_{eq}$)) than for another molecule, or at least 2-fold and typically at least 5-fold, 10-fold, 50-fold, 100-fold, or more, greater affinity ($K_a$ or $K_{eq}$)) than for another molecule. Typical conditions for detecting and determining binding affinity constants or for determining the selectivity of binding include physiological conditions, such as PBS (137 mM NaCl, 2.7 mM KCl, 10 mM phosphate buffer pH 7.4). Binding partners that specifically bind, bind with a binding affinity $K_a$ of typically at least about $10^7$ l/mol, $10^8$ l/mol or more. Generally, it refers to binding partners that selectively and specifically bind.

DETAILED DESCRIPTION OF THE INVENTION

Cytology is a branch of biology dealing with the study of the formation, structure, morphology, and function of cells. As applied in a laboratory setting, cytologists, cytotechnologists, and other medical professionals make medical diagnoses of a patient's condition based on visual examination of a specimen of the patient's cells. A typical cytological technique is a "pap smear" test, in which cells are scraped from a woman's cervix and analyzed microscopically in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as biopsies, whereby a tissue specimen is excised from the patient using specialized biopsy needles having spring loaded translatable stylets, fixed cannulae, and the like. Cell samples may be obtained from the patient by a variety of techniques including, for example, by scraping or swabbing an area, or by using a needle to aspirate body fluids from the chest cavity, bladder, spinal canal, or other appropriate area. In the processing of tissues for glass slides, the tissues are clinically removed from a patient and placed in a container that often contains a preservative and/or fixative and is then transported to the lab for further treatment or conditioning.

Once a specimen is prepared, fixed, and stained, the specimen may be manually visually inspected by a cytotechnologists, typically under magnification, and with or without various sources of illumination. Alternatively or additionally, automated machine vision systems have been adapted to aid cytological inspection. For example, an automated vision system may perform a preliminary assessment of the entire slide on which the specimen is disposed to alert the cytotechnologists to potentially the most relevant areas of the slide for close inspection, or may be used to rescreen specimens already analyzed by the cytotechnologists.

It is generally desirable that the cells on the slide have a proper spatial distribution, so that individual cells can be examined. A single layer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologists can more readily discern abnormal cells. The cells are also able to be counted to ensure that an adequate number of cells have been evaluated. Certain methods and apparatus for generating a thin monolayer of cells on a slide advantageous for visual examination are disclosed in U.S. Pat. No. 5,143,627 issued to Lapidus et al. and entitled "Method and Apparatus for Preparing Cells for Examination;" U.S. Pat. No. 5,240,606 issued to Lapidus et al. and entitled "Apparatus for Preparing Cells for Examination;" U.S. Pat. No. 5,269,918 issued to Lapidus et al. and entitled "Clinical Cartridge Apparatus;" and U.S. Pat. No. 5,282,978 issued to Polk, Jr. et al. and entitled "Specimen Processor Method and Apparatus," all of which are assigned to the assignee of the present invention and all of the disclosures of which are incorporated herein by reference in their entirety.

Filter interference or occlusion is a common problem when a multi-constituent solution must be filtered, especially when constituents have different fluid flow properties. Red blood cells rapidly lyse in some cell preservative solutions and, at above a certain concentration, the lysed components are known to interfere with the filtering and transferring of cervical epithelial and endothelial cells to microscope slides. The concentration of lysed red blood cells in solution can be grossly assessed by eye. When the concentration is observed to be too high or when a primary processed microscope slide has too many lysed red blood cell components, a widely accepted washing procedure using glacial acetic acid and centrifugation allows for satisfactory microscope slides to be made from a bloody specimen.

The method of the present invention provides the use of magnetic beads to remove lysed red blood cell components from a patient sample in a specimen container suspended in a specimen fluid without the need for elution, washing, or liquid removal. By using this method, lysed red blood cell components, and potentially other contaminants do not need to be removed but can be physically immobilized and isolated within a specimen container in a manner that will not interfere with subsequent specimen dispersion, filtering and slide processing.

The basic principle of magnetic separation is very simple. Magnetic carriers bearing an immobilized affinity or hydrophobic ligand or ion-exchange groups, or magnetic biopolymer particles having affinity to the isolated structure, are mixed with a sample containing target compound(s). Samples may be crude cell lysates, whole blood, plasma, ascites fluid, milk, whey, urine, cultivation media, wastes from food and fermentation industry and many others. Following an incubation period when the target compound(s) bind to the magnetic particles the whole magnetic complex is easily and rapidly removed from the sample using an appropriate magnetic separator. After washing out the contaminants, the isolated target compound(s) can be eluted and used for further work. A method for isolating metastatic malignant epithelial cells from blood has been reported (Hardingham et al. Cancer Research, 53, 3455-3458 (1993)).

It has been shown previously, with limited success, that cells tagged with micron-sized (0.1 mm) magnetic or magnetized particles can be removed or separated from mixtures using magnetic devices that either repel or attract the tagged cells. For the removal of desired cells, (i.e., cells which provide valuable information), the desired cell population is magnetized and removed from the complex liquid mixture (positive separation). In an alternative method, the undesirable cells, i.e., cells that may prevent or alter the results of a particular procedure, are magnetized and subsequently removed with a magnetic device (negative separation).

A faster, less expensive and less labor intensive procedure of removing lysed red blood cells from a specimen container containing cells of a patient specimen suspended in a specimen fluid, without the use of centrifugation and large volumes of reagents, would simplify the preparation of specimen slides from bloody specimens, improve the workflow of processing labs and possibly improve cell recovery by avoiding cell loss during supernatant removal.

The present invention describes a method for the removal of lysed red blood cells using magnetic beads which selectively bind to red blood cells. In one aspect of the present invention, a method comprising the steps of adding a complex comprising magnetic beads and a binder to a biological sample in a specimen container containing red blood cells or red blood cell fragments; allowing the complex to selectively bind to the red blood cells or red blood cell fragments in the specimen container; positioning a magnetic field in close proximity to the magnetic beads in the specimen container such that the beads are manipulated by the magnetic field; and manipulating the beads such that the red blood cells or red blood cell fragments separate from other cellular components of the patient sample in the specimen container is provided.

In a one embodiment, the magnetic beads are added to a specimen container containing cells of a patient specimen suspended in a specimen fluid when lysed red blood cells are present above a certain concentration. The magnetic beads are complexed with a binder which selectively binds to one or more components of red blood cells or red blood cell fragments. In a preferred embodiment, the binder is an aptamer specific to hemoglobin.

After allowing sufficient time for the complex to selectively binding to the red blood cells or red blood cell fragments within the specimen container, a magnetic field is brought within close proximity to the specimen container. The magnetic beads are either attracted (or repulsed) from the magnetic field. This manipulation of the magnetic beads allows for the concentration of the beads to a particular area of the specimen container. Once the magnetic particles with bound red blood cells or red blood cell fragments have been concentrated by magnetic force to a particular area of the specimen container, they can be physically immobilized in place in a manner that will not interfere with further processing of the biological specimen. In one embodiment of the present invention, the red blood cells or red blood cell fragments are manipulated from other cell components in the biological sample by removing the magnetic beads from the specimen container by the magnetic field after the magnetic beads have selectively bound to the red blood cells or the red blood cell fragments. In another embodiment of the present invention, the magnetic beads are paramagnetic.

In another aspect of the present invention, a method of separating red blood cells or red blood cell fragments from other cellular components in specimen container containing cells of a patient specimen suspended in a specimen fluid, the method comprising the steps of, adding a complex comprising magnetic beads and a binder which specifically binds to hemoglobin to a vial containing cells of a patient specimen suspended in a specimen fluid and red blood cells or red blood cell fragments, allowing the complex to selectively bind to hemoglobin in the red blood cells or red blood cell fragments and positioning a magnetic field in close proximity to the complex such that the complex move towards the magnet field is provided.

In yet another aspect of the present invention, a method of separating red blood cells or red blood cell fragments from other cellular components in specimen container containing cervical cells suspended in a preservative fluid, the method comprising the steps of, adding a complex comprising magnetic beads with aptamers specific to hemoglobin bound thereto to a specimen container containing cervical cells suspended in a preservative solution fluid and red blood cells or red blood cell fragments, allowing the complex to selectively bind to hemoglobin in the red blood cells or red blood cell fragments and positioning a magnet in close proximity to the complex such that the complex move towards the magnet; whereby the movement of the complex towards the magnetic results in the red blood cells or red blood cell fragments separating from other cellular components of the patient specimen suspended in the fluid in the specimen container is provided.

One known technique for selecting specimens for treatment is visually inspecting each vial and making a subjective judgment whether the particular specimen has too much blood and should be treated to reduce blood content. Thus, this technique is essentially based on how much blood is visible in the specimen.

FIG. 1 illustrates a preferred embodiment whereby an assembly is inserted manually by an end-user or automatically by an apparatus into a specimen vial which contains an excessive amount of blood and/or lysed red blood cell components. The assembly consists of an outer sleeve with integrated compartment containing paramagnetic beads, and inner sleeve which can be adjusted to release paramagnetic beads into solution and subsequently adjusted to physically immobilize paramagnetic beads with bound hemoglobin. The assembly contains an integrated compartment storing the paramagnetic beads with hemoglobin-binding complex which can be released into solution for binding with unwanted blood and blood components. The paramagnetic beads can then be retrieved by magnetic force from an external magnet and immobilized back in the same integrated compartment.

Figure 2:
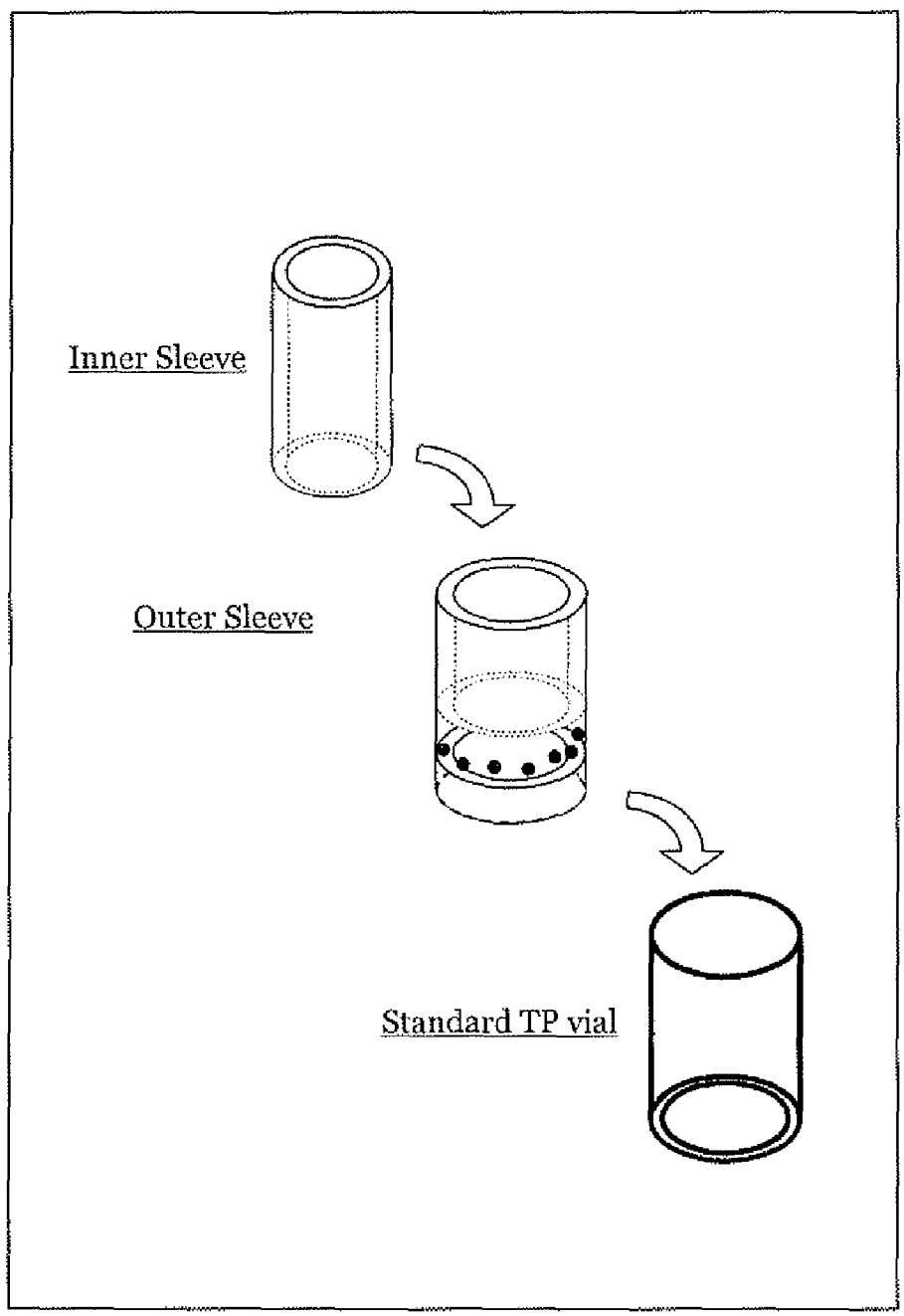
Figure 3:
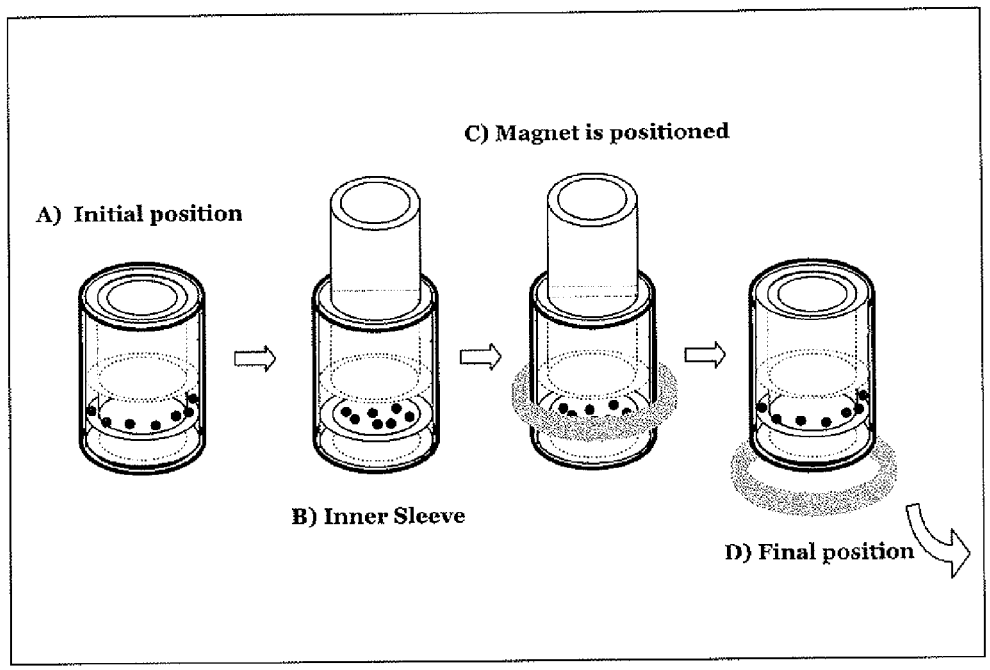

FIG. 2 and FIG. 3 provide more details of the preferred embodiment. FIG. 2 illustrates an Inner Sleeve which fits into an Outer Sleeve with an integrated compartment to store paramagnetic beads. The Inner and outer Sleeve assembly then fits into a standard TP sample vial. Note that the inner diameter of the Inner Sleeve is larger than the outer diameter of a filter. The inner sleeve may also have features, either permanent or removable, that facilitate the raising and lowering of the inner sleeve. FIG. 3 illustrates the steps to immobilize unwanted components in a TP sample. FIG. 3A shows the initial seated position of the Inner Sleeve. The assembly with the Inner Sleeve seated can be inserted into a standard TP vial containing a PreservCyt-based sample. FIG. 3B illustrates the Inner Sleeve raised up which allows the paramagnetic beads to be released into solution. FIG. 3C illustrates a ring magnet positioned around a TP vial such that the paramagnetic beads will be drawn out of solution and into the original integrated compartment. FIG. 3D shows the Inner Sleeve reseated after which the ring magnet can be removed.

As a result of this procedure the paramagnetic beads and bound hemoglobin are physically separated and immobilized and can not return into the specimen even with vigorous dispersion and aspiration of the PreservCyt-based sample.

An alternative embodiment utilizing a single piece sleeve. In this embodiment, the paramagnetic particles are provided in bulk in PreservCyt and a small amount is simply added (pipetted) into a specimen. After recapping the vial, binding of lysed red cell components to the paramagnetic beads can be facilitated by mixing (continuously if necessary). The beads are then separated and immobilized to the inner surface of the vial, near the bottom, by a magnetic force. While still in the presence of the magnetic field, the vial is uncapped, and a single sleeve is inserted into the vial, forming a seal against the vial bottom and entrapping the particles along the side within the sleeve indentation. The advantages of this embodiment are a simpler, more robust and less expensive design, larger inner diameter, the ability to mix, bind and magnetically separate within a capped vial, and less risk of the user touching or contaminating the specimen.

There are a variety of materials from which the sleeve(s) can be fabricated. Composite sleeves can also be envisioned whereby, for example, the majority of the single sleeve is made from polypropylene but the bottom and upper edges contain a more pliable, silicon-like material to facilitate forming a seal with the vial bottom and underside of the vial cap.

EQUIVALENTS

Those skilled in the art will recognize, or be able to ascertain using no more than routine experimentation, many equivalents to the specific embodiments of the invention described herein. The invention can be embodied in other specific forms without departing from the spirit or essential characteristics thereof. The present embodiments are therefore to be considered in all respects as illustrative and not restrictive. The scope of the invention is indicated by the appended claims, rather than by the foregoing description, and all changes which come within the meaning and range of equivalency of the claims are therefore intended to be embraced therein.

The invention claimed is:

1. A method of separating red blood cells or red blood cell fragments from other components of a biological sample in a specimen container the method comprising the steps of:
   i.) adding to a specimen container a biological sample containing red blood cells or red blood cell fragments, which specimen container comprises an inner sleeve and an outer sleeve defining an internal compartment therebetween containing magnetic beads, said magnetic beads comprising a binder capable of selectively binding to red blood cells or red blood cell fragments;
   ii.) removing said inner sleeve from said outer sleeve thus allowing said magnetic beads to come into fluid contact with said biological sample;
   iii.) allowing the magnetic beads to selectively bind to the red blood cells or red blood cell fragments in the specimen container;
   iv.) positioning a magnetic field in close proximity to the magnetic beads in the specimen container such that the beads are manipulated to the inner wall of the outer sleeve by the magnetic field; and
   v.) reinserting said inner sleeve into said outer sleeve such that the red blood cells or red blood cell fragments separate from other cellular components of the patient sample in the specimen container.

2. The method of claim 1 wherein the biological sample comprises cervical cells.

3. The method of claim 1 wherein the biological sample is suspended in a cell preservative solution.

4. The method of claim 1 wherein the magnetic beads are immobilized by the magnetic field to the inner surface of the specimen container within an integrated compartment.

5. The method of claim 1 wherein red blood cells or red blood cell fragments are manipulated from other cell components in the biological sample by removing the magnetic beads from the specimen container by the magnetic field after the magnetic beads have selectively bound to the red blood cells or the red blood cell fragments.

6. The method of claim 1 wherein the magnetic beads are paramagnetic.

7. A method of separating red blood cells or red blood cell fragments from other cellular components in specimen container containing cells of a patient specimen, the method comprising the steps of:
   i.) adding to a specimen container a patient specimen comprising red blood cells or red blood cell fragments, which specimen container comprises as inner sleeve and an outer sleeve defining an internal compartment therebetween containing magnetic beads, said magnetic beads comprising a binder capable of selectively binding to red blood cells or red blood cell fragments;
   ii.) removing said inner sleeve from said outer sleeve thus allowing said magnetic beads to come into fluid contact with said biological sample;
   iii.) allowing the magnetic beads to selectively bind to hemoglobin in the red blood cells or red blood cell fragments;

iv.) positioning a magnetic field in close proximity to the magnetic beads in the specimen container such that the magnetic beads are manipulated towards the magnet field;

whereby the manipulation of the magnetic beads towards the magnetic field results in the red blood cells or red blood cell fragments separating from other cellular components of the patient specimen in the specimen container.

8. The method of claim 7 wherein the patient sample comprises cervical cells.

9. The method of claim 7 wherein the patient sample is suspended in a cell preservative solution.

10. The method of claim 7 wherein the magnetic beads are immobilized by the magnetic field to the inner surface of the specimen container or within an integrated compartment.

11. The method of claim 7 wherein red blood cells or red blood cell fragments are separated from other cell components in the patient sample by removing the magnetic beads from the specimen container by the magnetic field after the magnetic beads have selectively bound to the red blood cells or the red blood cell fragments.

12. The method of claim 7 wherein the magnetic beads are paramagnetic.

13. A method of separating red blood cells or red blood cell fragments from other cellular components in specimen container containing cervical cells suspended in a preservative fluid, the method comprising the steps of:
   i.) adding to a specimen container a patient specimen comprising red blood cells or red blood cell fragments, which specimen container comprises as inner sleeve and an outer sleeve defining an internal compartment therebetween containing magnetic beads, said magnetic beads comprising aptamers specific to hemoglobin bound thereto;
   ii.) removing said inner sleeve from said outer sleeve thus allowing said magnetic beads to come into fluid contact with said biological sample;
   iii.) allowing the magnetic beads to selectively bind to hemoglobin in the red blood cells or red blood cell fragments;
   iv.) positioning a magnetic field in close proximity to the magnetic beads in the specimen container such that the magnetic beads are manipulated towards the magnet field;
   whereby the manipulation of the magnetic beads towards the magnetic field results in the red blood cells or red blood cell fragments separating from other cellular components of the patient specimen in the specimen container.

14. The method of claim 13 wherein the magnetic beads are immobilized by the magnet to the inner surface of the specimen container or within an integrated compartment.

15. The method of claim 13 wherein red blood cells or red blood cell fragments are separated from other cell components in the patient sample by removing the paramagnetic beads from the specimen container by the magnet after the magnetic beads have selectively bound to the red blood cells or the red blood cell fragments.

16. The method of claim 13 wherein the magnetic beads are paramagnetic.

* * * * *